United States Patent [19]

Swann

[11] 4,434,228

[45] Feb. 28, 1984

[54] IMMOBILIZATION OF BIOLOGICAL MATERIALS IN CONDENSED POLYALKYLENEIMINE POLYMERS

[75] Inventor: Wayne E. Swann, Columbia, Md.

[73] Assignee: Genex Corporation, Rockville, Md.

[21] Appl. No.: 370,242

[22] Filed: Apr. 20, 1982

[51] Int. Cl.$^3$ .................. C12P 13/22; C12P 13/20; C12N 11/08; C12N 11/04

[52] U.S. Cl. .................. 435/108; 435/109; 435/180; 435/182

[58] Field of Search ............... 435/174, 177, 180, 182, 435/108, 109

[56] References Cited

U.S. PATENT DOCUMENTS

| | | | |
|---|---|---|---|
| 3,791,926 | 2/1974 | Chibata et al. | 435/182 X |
| 3,830,699 | 8/1974 | Zaborsky | 435/180 |
| 3,859,169 | 1/1975 | O'Driscoll et al. | 435/182 |
| 4,182,695 | 1/1980 | Horn et al. | 435/180 X |
| 4,248,969 | 2/1981 | Lee | 435/176 |
| 4,355,105 | 10/1982 | Lantero, Jr. | 435/174 X |

FOREIGN PATENT DOCUMENTS 1396714 6/1975 United Kingdom.
2019410 10/1979 United Kingdom.

OTHER PUBLICATIONS

Jack et al., The Immobilization of Whole Cells, Advances in Biochem. Eng., vol. 5, 1977, (pp. 126-139).
Goldstein et al., The Chemistry of Enzyme Immobilization, Applied Biochemistry and Bioengineering, vol. 1, Immobilized Enzyme Principles, Academic Press, N.Y., 1976, (pp. 30-34).
Wykes, J. R., et al., *Biochim. Biophys. Acta* 286:260-68, (1972).
Horvath, C., *Biochim. Biophys. Acta* 358:164-77, (1974).
Sundaram, P. V., et al., *Clinical Chemistry* 24(10):1813-17, (1978).
Marshall, D. L., et al., *Carbohydrate Research* 25:489-95, (1972).
Chibata, D., ed., *Immobilized Enzyme Research and Development* (1978), pp. 31-33.

*Primary Examiner*—David M. Naff
*Attorney, Agent, or Firm*—Bernard, Rothwell & Brown

[57] ABSTRACT

Biological materials are immobilized within condensed polyalkyleneimine polymers. Condensation of the polymer is accomplished by bridging the amine groups of polyalkyleneimine polymer chains with a polycarboxylic acid, in the presence of a condensing agent.

34 Claims, No Drawings

IMMOBILIZATION OF BIOLOGICAL MATERIALS IN CONDENSED POLYALKYLENEIMINE POLYMERSd

This invention relates to a method for immobilizing biological materials. More particularly, the invention relates to the immobilization of biological materials by entrapping them within a polymer.

Biological materials such as enzymes or enzyme-producing microorganisms or cells, are often used as catalysts for synthetic reactions and for analytical techniques. Such catalysts are desirable because they operate with high specificity and efficiency under generally mild reaction conditions.

Because enzymes and other biocatalysts are generally water-soluble, they are suited for use in batch-type reaction systems. Reuse of such enzymes and other biocatalysts is limited, because of difficulties in recovering those materials from the spent reaction medium in active or usable form. Morever, the materials tend to remain in the prepared product as contaminants. In order to avoid these problems, methods have been developed to immobilize biological materials which exhibit catalytic activity on insoluble solid supports. Immobilization is intended to result in a stabilized biological material which can withstand the rigors of repeated or continuous use.

Several immobilization systems for biological materials have been reported. Enzymes have been immobilized by absorption onto insoluble materials such as charcoal, glass, cellulose, calcium phosphate gel, montmorillonite and organic ion-exchange resins among others. Immobilization has also been achieved by entrapment within starch and acrylamide gels, covalent attachment between enzymes and insoluble organic polymers, as well as covalent attachment between enzyme molecules themselves.

The processes of the prior art often result in products of reduced enzymatic activity, when compared with that of the corresponding unbound biological material. These biological materials are known to be sensitive to thermal and chemical denaturation or inactivation. The loss of biological activity often results when immobilizing operations are carried out under harsh conditions which can be particularly problematic when polymer condensation reactions are involved. Furthermore, the products resulting from prior art methods are often disadvantageous with respect to their hydrophilicity, strength, durability, and porosity.

It has now been discovered that biological materials can be immobilized in a simple economical manner while maintaining a high degree of their catalytic activity. The method of the present invention produces an insolubilized biological material composite which contains biological material entrapped within a condensed polyalkyleneimine polymer. Although the composite is prepared by conducting the polymer condensation reactions in the presence of the biological material, the reaction conditions are so mild that very little loss of activity occurs. Such composites exhibit excellent strength and durability. Furthermore, the hydrophilicity of these materials can be adjusted by varying the extent of condensation. The method of the present invention produces a composite which can be separated from reaction mixtures by simple filtration, or used in continuous reaction processes such as those wherein a reacting substrate flows through a packed column reactor.

In accordance with the method of the present invention, a polyalkyleneimine polymer is condensed with a condensing amount of a polycarboxylic acid in the presence of a condensing amount of a condensing agent, wherein said biological material is mixed with said polyalkyleneimine polymer during said condensation reaction. Addition of the condensing agent results in the formation of an insolubilized biological material composite, wherein the biological material is immobilized within the polymer. Immobilization of biological material within the polymer can occur by physical entrapment as well as by covalent bonding between the polyalkyleneimine or the condensing agent and reactive groups on the biological material. For example, the biological material can be immobilized through covalent linkage, since amine and carboxyl groups of the biological material can substitute for either an amine group on the polyalkyleneimine or a carboxylic group on the polycarboxylic acid and ultimately become covalently linked to the polymer.

The method of the present invention allows the preparation of a wide variety of biological material composites which can differ in hydrophilicity, strength, durability, and porosity. Decreasing the extent of condensation can result in a composite having greater solubility in water. The addition of multifunctional crosslinking agents can increase the strength and durability of the polymer-biological material composite, where the additional functional groups further condense the polyalkyleneimine polymer.

The overall porosity of the matrix can be increased by the addition of a water-soluble particulate material to the polymer mixture prior to complete condensation. The dry material is subsequently removed by the addition of water after condensation, which dissolves the solid. The portion of the composite formerly displaced by the solids are left empty, thus increasing the porosity of the matrix. Any water-soluble particulate material that does not adversely affect the polymer or biological material significantly may be employed for increasing the porosity of the mixture. Water soluble polycarboxylic acids, such as those reacted with the uncondensed polyalkyleneimines, are particularly suited to increasing matrix porosity, since excess amounts utilized to increase porosity do not substantially interfere with the condensation reactions.

Polyalkyleneimines used in the method and composites of the present invention are polymers, which can be synthesized by the acid-catalyzed addition polymerization of alkyleneimine monomers. Such polymers generally vary between 30,000 and 100,000 in molecular weight, depending on reaction conditions, and preferably have a branched chain structure.

Polyethyleneimine (PEI) is a preferred polyalkyleneimine, because it is currently readily available at relatively low cost, and it functions well in the condensation reactions employed in the present method. Polyethyleneimine is produced by ring-opening polymerization of ethyleneimine in the presence of catalysts, such as mineral acids. The polymer is highly branched and contains primary, secondary and tertiary amino groups. PEI is water-soluble, and upon condensation of the polymer chains, a water-insoluble product results. A highly efficient method of condensation utilizes a polycarboxylic acid (PCA) to bridge amine groups on adjacent PEI chains. Condensing agents, preferably carbodiimides, readily effects the condensation. The reactions involved in making the condensed polyethyleneimine of the present invention are illustrated below:

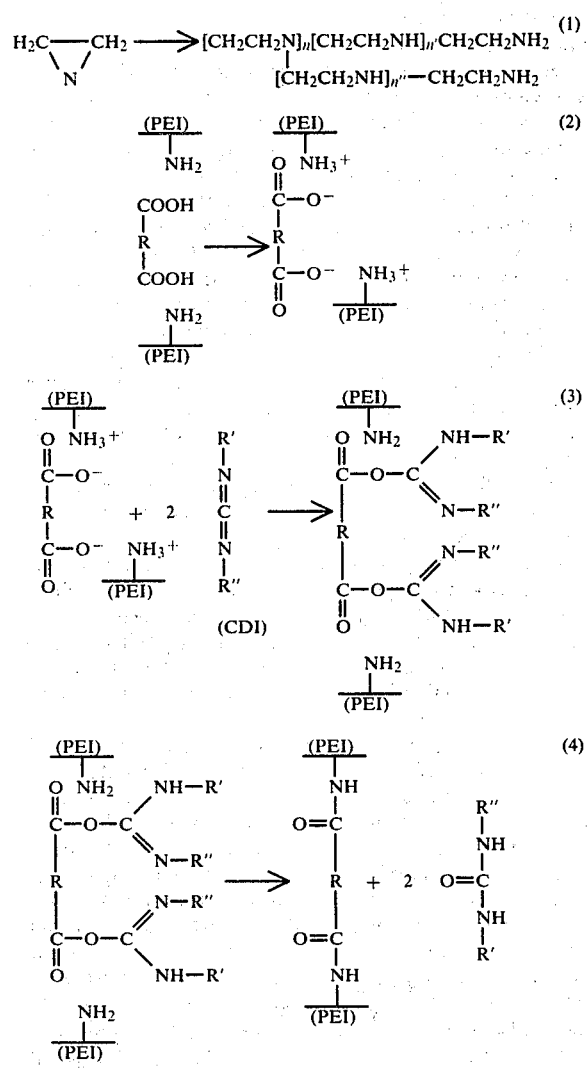

Reaction (1) illustrates the polmerization of ethyleneimine to form PEI having a branched-chain structure, wherein n and n' are integers greater than 0 and n" may be 0 (indicating that the [CH₂CH₂NH] group is absent) or greater than 0. Reaction (2) shows the formation of a salt of the amine groups of PEI with a polycarboxylic acid, wherein R can be a direct bond or a substituted or unsubstituted hydrocarbon group, for example, a straight or branched chain hydrocarbon optionally containing alicyclic, olefinic or aromatic groups, as well as various functional groups, such as hydroxyls, carbonyls, carboxylic groups, amines, nitriles, amides, esters and the like, which do not deleteriously affect the condensation reaction, the biological materials or the resulting composite. Such groups can vary widely, to provide a wide range of useful polycarboxylic acids, as hereinafter discussed. Reactions (3) and (4) show the condensation of the PEI and polycarboxylic, using a carbodiimide condensing agent. R' and R" are hydrocarbon groups, which, along with other reactants and conditions of the illustrated reactions, are described more fully below.

In general, polycarboxylic acids suited for use in the present invention may be substituted or unsubstituted carboxylic acids having at least two carboxylic groups. Preferably, the polycarboxylic acids are water-soluble, so that they may be utilized to increase the porosity of the composite, as well as for condensing the polyalkyleneimine. Examples of polycarboxylic acids that can be employed in the methods and composites of the present invention include adipic, azelaic, 1,11-undecanedioic, 1,12-dodecanedioic, traumatic, pentadecanedioic, hexadecanedioic, sebacic, suberic, glutaric, malonic, pimellic, succinic, malic, maleic, glutamic, aspartic, oxalic, fumaric, polyaspartic, and the like. Dicarboxylic acids are preferred for use in the present invention and include maleic acid, succinic acid, glutaric and adipic acid. Higher polycarboxylic acids include any substance that contains two or more carboxylic acid groups, e.g. high molecular weight polymeric materials, such as polyaspartic acid, having a molecular weight of from about 5,000 to 70,000. The condensation reactions are generally exothermic, therefore, the reaction mixtures are advantageously cooled to a temperature that is not deleterious to the biological material being immobilized, e.g., about 37° or lower.

The molar ratio of polycarboxylic acid to polyalkyleneimine (PCA:PAI) can vary widely, because of the variation in molecular weight of the reactants. Generally, the polycarboxylic acid can be employed in any condensing amount, and the ratio of PCA to PAI generally ranges from 1:20 to 1:0005. Where polycarboxylic acid is added to increase the porosity of the composite of the present invention, a considerable molar excess of polycarboxylic acid is often employed.

In preparing the composites, any order of addition of ingredients may be employed. For example, the biological material to be immobilized may be introduced at any time prior to solidifying of the polymer, but it is preferably added after the addition of the polycarboxylic acid to the polyalkyleneimine. A preferred method for preparing the composites of the present invention is to add a condensing amount of a polycarboxylic acid to the polyalkyleneimine under prepolymerizing conditions to form a water-soluble prepolymer. The prepolymer is generally a viscous liquid, to which biological material can conveniently be added and maintained in suspension during the condensation reaction. The condensing agent is then added to effect condensation and solidification of the polymer-biological material composite. The pH of the reaction mixture is maintained at a level which does not substantially inactivate or adversely affect the biological material. The pH can range from about 2 to 12 and preferably ranges from about 5 to 10.

The amount of biological material added to the polymer can vary according to the specific end use of the biological material composite. Generally it ranges from about 0.001 to 10 g (dry weight basis) per gram of polyalkyleneimine used, preferably from about 0.1 g to 5 g per gram of PAI. The biological material can include enzymes, microbial cells, antigens, antibodies, antibiotics, carbohydrates, coenzymes, plant cells, animal cells, bacteria, yeasts, fungi, tissue cultures or mixtures thereof. Enzymes can be added to the reaction mixture in aqueous solution or powdered form, preferably the latter. Cells can be added in the form of wet paste or dry particulates.

As noted above, to effect condensation of polyalkyleneimine chains through polycarboxylic acids, a condensing agent is advantageously employed. Generally, any condensing agent that catalyzes or facilitates the reaction of amines and carboxylic acids can be used. Examples of such condensing agents include N-ethyl-5-phenyl-isoazolium-3-sulfonate, n-ethoxycarbonyl-2-ethoxy-1,2-dihydroquinoline, and various carbodiimides. Carbodiimide condensing agents are preferred, and such agents generally include compounds of the formula R'—N=C=N—R" where R' and R" are hydrocarbon groups containing from 3 to about 20 carbon atoms, preferably from about 5 to about 12 carbon atoms. Such carbodiimide condensing agents include 1-ethyl-3,3-dimethylaminopropyl carbodiimide, dicyclohexyl carbodiimide, 1-cyclohexyl-3-(2-morpholinoethyl) carbodiimide metho-p-toluene sulphonate, and salts thereof. Carbodiimide condensing agents are added to the reaction mixture in a condensing amount, which generally is substantially a stoichiometric amount; e.g. from about 0.2 to 3 times, preferably from about 0.5 to 1.5, a stoichiometric amount. Each carbodiimide molecule reacts with a single acid group of the polycarboxylic acid. For example, carbodiimide to dicarboxylic acid molar ratios of about 2:1 are generally used in the method of the present invention; however, much lower molar ratios are used if excess polycarboxylic acid is employed to increase the porosity of the composite. Upon addition of the condensing agent at room temperature, noticeable polymerization results within thirty seconds, and is generally complete within about two hours.

Specific embodiments of the present invention can additionally involve post treatment of the composite with an amine cross-linking agent to impart additional stability and strength. Such cross-linking agents include glutaric dialdehyde, diisocyanates, polyisocyanates, 2,4,6-trichloro-S-triazine, bisoxirane, bisimidate, divinylsulfone, 1,5-difluoro-2,4-dinitrobenzene, and the like. Glutaric dialdehyde is preferred for this purpose.

By the use of the described methods of the present invention, it is possible to immobilize a wide variety of biological materials to produce novel biocatalytic composites. In the following examples, the immobilization procedures are described in greater detail. These examples describe the manner and process of making and using the invention and set forth various embodiments of the invention, but are not to be construed as limiting.

EXAMPLE I

Polyethyleneimine (4.0 grams of a 30% aqueous solution) was mixed with succinic acid (2 grams). The mixture temperature increased to 45° C. and was allowed to cool to 22° C. At this point the resulting mixture was a water-soluble prepolymer. A cell-free aqueous aspartase solution was prepared in accordance with the procedures of Example I, paragraph 1 of copending U.S. application Ser. No. 311,618, filed Oct. 15, 1981. One ml of the aspartase solution was then added to the water-soluble prepolymer mixture which was subsequently condensed by the addition of 1-ethyl-3,3-dimethylaminopropyl carbodimide hydrochloride in powdered form. The addition of the condensing agent resulted in polymerization within thirty seconds yielding of a fixed biological material composite in gel form. The gel was then ground in a mortar with a pestle to yield small particles.

EXAMPLE II

The particulate biological material composite of Example I was placed in fifty milliliters of a solution of 1 molar ammonium fumarate, 1 millimolar magnesium sulfate, pH 8.5, and the mixture was stirred for 30 minutes. The solution was filtered, and the procedure was repeated twice, with the second stirring continuing for sixteen hours.

The particles were then placed in 35 ml. of the same ammonium fumarate substrate solution at 37° C. After one hour, the biologically active particles were found to have converted 1509 $\mu$ moles of ammonium fumarate to L-aspartic acid. The particles were then rinsed with fresh substrate, partially dried and again placed in 35 ml. of ammonium fumarate substrate solution at 37° C. Again, after one hour, 1509 $\mu$ moles of ammonium fumarate had been converted to L-aspartic acid, indicating that the biological activity of the composite had been maintained.

EXAMPLE III

Polyethyleneimine (6 g) was mixed with powdered succinic acid (3 g) and allowed to cool to room temperature. A wet cell paste containing about 75% water by weight was prepared from fresh aspartase-containing *E. coli* by the following procedure. A fermentation medium was prepared by dissolving in one liter of water, 24 grams of yeast extract, 30 grams of fumaric acid, 2 grams of sodium carbonate, 2 mM magnesium sulfate, and 0.1 mM calcium chloride, and the pH was adjusted to about 7.2 with ammonium hydroxide. This medium was inoculated with 1 ml. of a culture of *E. coli* (ATCC No. 31976) that had been incubated for 12–16 hours at 37° C. in a peptone medium containing 0.5 percent monosodium glutamate. The inoculated medium was incubated for 12–14 hours at 37° C. The cells were harvested by centrifuging at 5000 rpm for 30 minutes. Three grams of the wet cell paste were added evenly to the prepolymer. 1-Ethyl-3,3-dimethylaminopropyl carbodimide hydrochloride (EDAC-HCl) (2 g) was then added and mixed for about one minute. The resulting mixture polymerized. After standing at room conditions for 2 hours the polymerized mixture was ground into particles. The gel particles were then soaked in an aqueous solution of 1.5 M ammonium fumarate, pH 8.5 at 22° C. This soaking was repeated with fresh substrate, then the gel was rinsed with a third aliquot of substrate. The gel was assayed for aspartase activity by measuring the disappearance of fumaric acid on a spectrophotometer at 240 nm. The gel particles were continuously stirred in a room temperature batch reactor for 1 hour in the presence of 75 ml of substrate. A conversion of about 98% was observed which corresponds to the known equilibrium of the reaction. The reaction was then repeated with similar results. Table I shows the decreases in ammonium fumarate concentration with time for the 2 batch reactions.

TABLE I

| Decrease in Substrate Concentration Over Time | | |
|---|---|---|
| Reaction | mg/ml ammonium fumarate | |
| time (min) | Run 1 | Run 2 |
| 0 | 174.0 | 174.0 |
| 15 | 77.9 | 78.6 |
| 30 | 37.6 | 36.5 |
| 60 | 1.8 | 2.7 |

EXAMPLE IV

One half of the gel used for the batch reactions of Example III was loaded into a 0.9 cm diameter column.

The resulting bed volume was 14 cc. A 1.5 M ammonium fumarate solution (22° C.; pH 8.5) was pumped through the column (upflow) at 1 space volume (SV) per hour (14 cc/hour) continuously for 70 days. Samples of the effluent were analyzed for disappearance of ammonium fumarate. The results are shown in Table II below. The initial conversion rate of the column was 190 g ammonium fumarate/1 bed volume/hr. at 22° C. and this rate fell to 168 g/1/hr. after 70 days of continuous operation. This represents a loss of productivity of only 12%.

TABLE II

| Day | % Conversion |
| --- | --- |
| 1 | 95.4 |
| 2 | 95.9 |
| 22 | 96.8 |
| 38 | 93.1 |
| 70 | 84.2 |

EXAMPLE V

PEI (3 grams) was mixed with 1.4 grams of succinic acid and allowed to cool to room temperature. One and one-half grams of harvested yeast cells, *Rhodotorula rubra* (ATCC-4056) containing phenylalanine ammonia-lyase activity were mixed into the mixture. One gram of 1-ethyl-3,3-dimethylaminopropyl carbodiimide hydrochloride was then added and mixed for 1 minute. The resulting mixture polymerized into a stiff gel-like material. The gel was ground in a mortar with a pestle then soaked, washed and resoaked in a substrate solution containing t-cinnamic acid and ammonium hydroxide at a pH of 9.5. The washed material remained red in color, whereas the wash solution was visually colorless and clear, which indicated that the red *R. rubra* cells remained in the composite particles. After 39 hours, the resulting reaction mixture was filtered and the filtrate was analyzed for L-phenylalanine. The concentration of phenylalanine in the filtrate was found to be approximately 0.5 grams/liter.

EXAMPLE VI

A series of experiments was conducted to investigate the effects of the polycarboxylic acid on the system. For each experiment, the procedure of Example III was followed, with the following exceptions: 3 grams of PEI, 2 grams of polycarboxylic acid, 1.5 grams of EDAC.HCl, and 1 gram of *E. coli* cell paste were used. A separate immobilization reaction was conducted for each of the following polycarboxylic acids: azelaic, 1,11-undecanedioic, 1,12-dodecanedioic, traumatic, pentadecanedioic, hexadecanedioic, sebacic, suberic, glutaric, malonic and pimellic. Each polycarboxylic acid was effective for the immobilization of the cells. Six of the resulting composites, ranging from low to high molecular weight (glutaric, pimellic, sebacic, 1,11-undecanedioic, 1,12-dodecanedioic, and suberic) were selected for analytical testing of their biological activities. All of the six composites were effective in converting ammonium fumarate to aspartic acid.

EXAMPLE VII

PEI (5 grams) was mixed with 1 gram of polyaspartic acid, then 1.5 grams of EDAC-HCl was added. Polymerization resulted within 5 minutes, forming a tough gel-like polymer that was insoluble in water.

EXAMPLE VIII

Tryptophan synthetase (EC 4.2.1.20) is an enzyme that can be derived from a variety of microbial sources, e.g. from Proteus, Erwinia, Escherichia, Psudomonas and Aerobacter microorganisms. (See *Methods in Enzymology, Chem. Tech. Rev.* Academic Press (1980)). This enzyme can be used to catalyze the conversion of indole and serine to tryptophan. This example describes the immobilization of a tryptophan synthetase enzyme extract from *E. coli* cells. PEI (4 g) and succinic acid (2 g) were mixed, and the mixture was allowed to cool to room temperature. One-half milliliter of enzyme extract was added to the mixture, followed by 1.5 g of EDAC.HCl. The resulting gel was ground with particles and thoroughly washed. The resulting particles were then added to a substrate solution containing 0.05 M L-serine and 0.05 M indole. The composite was found to be effective in converting the substrate to L-tryptophan in the reaction mixture in two successive runs.

I claim:

1. A method for immobilizing a biological material by preparing an insolubilized biological material composite, comprising condensing a polyalkyleneimine polymer with a condensing amount of a polycarboxylic acid in the presence of a condensing amount of a condensing agent, wherein said biological material is mixed with said polyalkyleneimine polymer during said condensation reaction.

2. The method of claim 1, wherein the polyalkyleneimine polymer is selected from the group consisting of polyethyleneimine, polypropyleneimine, polybutyleneimine and polypentyleneimine.

3. The method of claim 1, wherein the polyalkyleneimine polymer is polyethyleneimine.

4. The method of claim 1, wherein the polycarboxylic acid is a dicarboxylic acid.

5. The method of claim 1, 2 or 3 wherein the polycarboxylic acid is selected from the group consisting of adipic, azelaic, 1,11-undecanedioic, 1,12-dodecanedioic, traumatic, pentadecanedioic, hexadecanedioic, sebacic, suberic, glutaric, malonic, pimellic, succinic, malic, maleic, glutamic, aspartic, oxalic, fumaric, and polyaspartic.

6. The method of claim 1, 2 or 3 wherein the polycarboxylic acid is succinic acid.

7. The method of claim 1 wherein the condensing agent is selected from the group consisting of N-ethyl-5-phenylisoxazolium-3-sulfonate, N-ethoxycarbonyl-2-ethoxy-1,2-dihydroquinoline.

8. The method of claim 1 wherein the condensing agent is a carbodiimide condensing agent.

9. The method of claim 8, wherein the carbodiimide condensing agent is 1-ethyl-3,3-dimethylaminopropyl carbodiimide, dicyclohexyl carbodiimide, 1-cyclohexyl-3-(2-morpholinoethyl) carbodiimide metho-p-toluene sulfonate, or a salt thereof.

10. The method of claim 1, wherein the carbodiimide condensing agent is 1-ethyl-3,3-dimethylaminopropyl carbodimide or a salt thereof.

11. The method of claim 5 wherein the condensing agent is 1-ethyl-3,3-dimethylaminopropyl carbodiimide or a salt thereof.

12. The method of claim 1, 2, 3 or 4, wherein the molar ratio of polyalkyleneimine to polycarboxylic is from about 1:20 to 1:0005.

13. The method of claim 12, wherein the condensing agent is employed in an amount ranging from about 0.2 to 3 times stoichiometric, relative to the polycarboxylic acid.

14. The method of claim 12, wherein the condensing agent is employed in an amount ranging from about 0.5 to 1.5 times stoichiometric relative to the polycarboxylic acid.

15. The method of claim 1, 2, 3 or 4 wherein the polyalkyleneimine and polycarboxylic acid are first mixed, then the biological material is added, then the condensing agent is added.

16. The method of claim 1, wherein the biological material immobilized is an enzyme.

17. The method of claim 1, wherein the biological material immobilized comprises whole cells.

18. The method of claim 17, wherein the whole cells are E. coli cells which contain aspartase.

19. The method of claim 9, wherein the biological material is aspartase.

20. The method of claim 1, wherein the biological material comprises phenylalanine ammonia-lyase.

21. The method of claim 1, wherein the biological material comprises tryptophan synthetase.

22. The method of claim 1, further comprising post treatment of the insolubilized biological material composite with an amine crosslinking agent to impart additional strength and stability to the composite.

23. The method of claim 22, wherein the amine crosslinking agent is selected from the group consisting of glutaric dialdehyde, diisocyanates, polyisocyanates, 2,4,6-trichloro-S-triazine, bisoxirane, bisimidate, divinylsulfone, and 1,5-difluoro-2,4-dinitrobenzene.

24. The method of claim 22, wherein the amine crosslinking agent is glutaric dialdehyde.

25. An insolubilized biological material composite comprising a biologically active material immobilized within a condensed polyalkyleneimine polymer, wherein amino groups on the polyalkyleneimine chains are bridged by a polycarboxylic acid.

26. The composite of claim 25, wherein the biologically active material is selected from the group consisting of enzymes, antigens, antibodies, antibiotics, carbohydrates, coenzymes, plant cells, bacteria, yeast, fungi and tissue cultures.

27. The composite of claim 25, wherein the biologically active material is selected from the group consisting of enzymes and whole cells.

28. The composite of claim 25, wherein the biologically active material is aspartase.

29. The composite of claim 25, wherein the biological material are whole cells of E. coli which contain aspartase.

30. The composite of claim 25, wherein the biological material comprises phenylalanine ammonia-lyase.

31. The composite of claim 25, wherein the biological material comprises tryptophan synthetase.

32. A method for producing aspartic acid, comprising contacting, under aspartic acid-producing conditions, a substrate, containing ammonium fumarate, with an insolubilized biological material composite of aspartase or aspartase-containing microbial cells immobilized within a condensed polyalkyleneimine polymer, wherein amino groups on the polyalkyleneimine polymer chains are bridged by a polycarboxylic acid.

33. A method for producing phenylalanine, comprising contacting, under phenylalanine-producing conditions, a substrate, containing t-cinnamic acid and ammonia, with an insolubilized biological material composite of phenylalanine ammonia-lyase or phenylalanine ammonia-lyase-containing microbial cells immobilized within a condensed polyalkyleneimine polymer, wherein amino groups on the polyalkyleneimine polymer chains are bridged by a polycarboxylic acid.

34. A method for producing tryptophan, comprising contacting, under tryptophan-producing conditions, a substrate, containing indole and serine, with an insolubilized biological material composite of tryptophan synthetase or tryptophan-synthetase-containing microbial cells immobilized within a condensed polyalkyleneimine polymer, wherein amino groups on the polyalkyleneimine polymer chains are bridged by a polycarboxylic acid.

* * * * *